United States Patent [19]

McCann et al.

[11] Patent Number: 5,599,795

[45] Date of Patent: Feb. 4, 1997

[54] METHOD FOR TREATMENT OF IDIOPATHIC INFLAMMATORY BOWEL DISEASE (IIBD)

[76] Inventors: Michael McCann, 7711 Edgewood Dr., Seven Hills, Ohio 44131; Richard S. Abrams, 2016 Wilmette Ave., Wilmette, Ill. 60091

[21] Appl. No.: 264,052

[22] Filed: Aug. 19, 1994

[51] Int. Cl.$^6$ .......................... A61K 31/70; A61K 31/43; A61K 31/395; A61K 31/415

[52] U.S. Cl. .......................... 514/31; 514/192; 514/198; 514/210; 514/398

[58] Field of Search .............................. 514/31, 192, 198, 514/210, 398

[56] References Cited

U.S. PATENT DOCUMENTS 5,214,066  5/1993  Szabo ................................. 514/423
5,229,374  7/1993  Burton et al. ........................... 514/62
5,443,826  8/1995  Borody ................................. 424/93.3

OTHER PUBLICATIONS

CA 108: 49096, Ohkusa et al., 1987.

*Primary Examiner*—Kimberly Jordan
*Attorney, Agent, or Firm*—Paul Y. Feng

[57] ABSTRACT

A new method for the prevention and treatment of Idiopathic inflammatory Bowel Disease (IIBD), including Crohn's Disease and Ulcerative Colitis, in human patients is provided. The key steps include sterilizing the intestinal tract with multiple antibiotics to kill the pre-existing bacterial flora, and replacing the latter with different, select, well-characterized bacteria taken from normal humans. The new microflora serve to generate more normal metabolic and immune responses, remitting thereby the IIBD.

3 Claims, No Drawings

METHOD FOR TREATMENT OF IDIOPATHIC INFLAMMATORY BOWEL DISEASE (IIBD)

FIELD OF THE INVENTION

This invention relates to an improved method for preventing and treating idiopathic inflammatory bowel disease (IIBD), including Crohn's Disease and Ulcerative Colitis in human patients by sterilizing the intestinal tract by the use of multiple antibiotics, and the use of select, well-characterized intestinal bacteria taken from normal humans to replace the patient's intestinal bacteria.

DESCRIPTION OF THE PRIOR ART

Idiopathic Inflammatory Bowel Disease (IIBD) is a disease of unknown etiology, manifested by destruction of the wall of the intestine, and an abnormal and excessive immune response to a person's own intestinal cell molecules. Until now, all therapies of this disease have been directed toward suppression of the general immune response, often with poor success, and always with little or no selectivity, and with unwanted and sometimes dangerous consequential side effects. The original defect is thought to be genetic, but penetrance of the abnormal gene or genes is believed to be caused by phenomena occurring inside the lumen of the intestine. Every person normally has numerous genera and many more species as well as particular strains of bacteria in his/her intestinal tract. These strains are called the indigenous microflora. Their purpose is not well understood. One theory of the etiology of IIBD is that the immune system may be unusually stimulated by one or another strain of one's own intestinal indigenous bacterial microflora, and that the configuration of those antigenic bacterial molecules may be similar to the configuration of that person's own cells' molecules (molecular mimicry). As a result, there would be a "cross-reactivity", with the immune system attacking and destroying the person's own similarly-shaped cellular protein and/or glycoprotein molecules. A second theory is that toxic metabolic products are produced by one's indigenous microflora which alter or destroy one's intestinal cells. A third theory is that some of the natural intestinal digestive secretions coming from the liver and pancreas are not properly neutralized by one's indigenous microflora, so the intestinal epithelium continues to be exposed to their erosive and digestive process. We believe that by suppressing or killing all, or the vast majority of the indigenous microflora of the intestinal tract, and replacing them (a "re-florestation") with a selection of known, specific, non-pathogenic bacteria, there will be subtle, but significant changes in the composition of the indigenous microflora. Changes in the metabolic pathways, processes, products and functions of fats, proteins, carbohydrates, and of intestinal secretions will then follow. In addition, the new bacteria will also offer different molecular configurations to the immune receptors. With the absence or change of immune stimulation, the destructive process will stop, and there will no longer be pathological inflammation of the intestinal wall.

SUMMARY OF THE INVENTION

The invention is directed to a method of preventing and treating IIBD in humans, comprising replacing the former (presumed pathologically antigenic) bacterial flora with selected, new, non-pathogenic human intestinal bacteria. There should be a normalization of the immune responses, and a cessation of inflammation. Compared with other methods to reduce or stop inflammation, this method is non-toxic to the human or animal, and offers the hope of completely stopping inflammation at the molecular level.

DETAILED DESCRIPTION OF THE INVENTION

In order to attempt to sterilize the intestinal wall and intestinal lumenal contents, concurrent administration of several antibiotics is necessary. Several combinations of antibiotics may be used. Vancomycin, metronidazole, an aminoglycoside (such as gentamycin), a monobactam (such as aztreonam), and an anti-fungal agent (such as nystatin); or a third generation cephalosporin (such as cefaperzone), nystatin metronidazole, ampicillin-sulbactam (or ampicillin-clavulanate), must be used for 72 to 120 hours (days 2 through days 4, 5, or 6) depending on the severity of the inflammation and infection, given orally or parenterally. All antibiotics are given in standard doses according to weight, age, or surface area of the patient. Prior to antibiotic administration, the patient's room (not in a hospital, to avoid possible contamination with antibiotic-resistant bacteria) is disinfected by using any standard bactericidal agent. Floors, walls, window sills, table, chairs, etc. are swabbed with this agent each 24 hours (from day 1 through day 10). Bedsheets and blankets are washed just prior to use. Air entering the room is filtered with a HEPA-type filter system, although some fresh air is permitted. Vents should be closed if their contained air comes from another part of the building thought to harbor potential pathogenic bacteria. The intestine is cleaned, using any standard cathartic or laxative (during day 1). Magnesium citrate or "Go-LYTELY" are two examples. Enemas are not given. Oral rinses of a germicidal solution, such as chlorhexidine gluconate are given every 2 hours (staring after the cathartics, on day 1 through days 11, 12, or 13). Teeth are brushed 4 times a day, using brushes sterilized by microwave heating before each usage, (without tooth paste, followed by chlorhexidine rinses). Facial cleansing is done 4 times a day with ordinary soap and water. On day 1, after the bowel has been emptied from the laxatives, a germicidal soap shower is taken, including hair wash. Clean masks, gowns, and caps are worn by all personnel in contact with the patient or supplies, from day 1 through days 11, 12 or 13. Clear, sterile liquids (such as soda pop, water, and elemental preparations, such as Vivonex) are given, starting from day 1 (after bowel evacuation) through days 4, 5 or 6. Diet is increased to sterile, full liquids on days 4, 5 or 6 (beginning 6 hours after the last antibiotic dosage), for 24 hours. Thereafter, diet consists of solid, sterile, normal food. Sterilization of food is achieved by microwaving, or boiling, or frying, or broiling, etc., at temperatures greater than 212 degrees F. for a least 5 minutes. Some easily sterilized foods are: hamburgers, potatoes, cooked vegetables, rice, spaghetti, and soups. Sterile solid diet is continued until day 15, 16, or 17.

Bacteria are obtained and maintained in freeze-dried (lyophilized) form, or frozen in liquid nitrogen, or in suitable culture media. The anaerobic bacteria require expert handling to avoid contamination from opportunistic bacteria to avoid damage from oxygen. Suitable sterile, commercially available oxygen-free solid or liquid culture media tubes or bottles are used to maintain the mixture of anaerobes. Aerobes are maintained with the same precision, in suitable sterile, solid or liquid, culture media tubes or bottles (for example, tryptocase soy broth) containing normal air. Materials: Specific strains of the following genera and species of bacteria will be used to accomplish the "re-florestation": *Bacteroides vulgatus, distasonis, stercoris, ovatus, caccae,* and *uniformis; Bifidobacterium adolescentis, longum,* and *bifidum; Eubacterium aerofaciens, rectale; Fusobacterium prausnitzii; Ruminococcus obeum, bromii, gnavus; Lactobacillus acidophilus, leichmannii; Streptococcus oralis; Escherichia Coli* (Pingel, Nissl 1917, and other strains).

After ingestion of ½ to 1 teaspoon of sodium bicarbonate (heat treated/new box carefully opened) to neutralize stomach acid, at least approximately 10 to the 8th power of each bacteria in the mixture, in isotonic saline, is swallowed (separately or together) 3 times per day for 1 week (days 4, 5, or 6 through 11, 12, or 13). Rectal infusions of the same bacteria are given twice per day for 5 days. Sterile gloves are used to manipulate a sterile catheter and/or syringe for the rectal insertions. The anus is first swabbed with a germicidal preparation (such as povidone-iodine, 10%). The patient is placed upside down, over a chair, and tilted side to side for 30 minutes, so that gravity will disperse the infusion as proximally as possible. Approximately 100 cc of sterile isotonic saline is used to suspend the infusion mixture of bacteria.

The patient's general medical condition, blood pressure, pulse, temperature, is monitored throughout the procedure, by appropriately trained and motivated staff. Four days after stoppage of the antibiotics, the patient is allowed to leave his or her room. All medicine taken previously for this IIBD procedure are allowed to be gradually withdrawn over a period of time, being determined by the clinical picture. Maintenance doses of the same bacteria should be taken once per week by mouth for an unlimited length of time

We claim:

1. A method of preventing or treating idiopathic inflammatory bowel disease, Crohn's Disease or ulcerative colitis in a human patient comprising administering to said patient a composition comprising at least one antibiotic agent and at least one anti-fungal agent to sterilize the intestine of said patient and then infusing orally and rectally to said patient a specific bacteria composition to establish colonization of the intestine whereby the pathological immune response is normalized and inflammation ceases.

2. The method of claim 1, wherein said antibiotics and anti-fungal composition consist essentially of ampicillin-sulbactam; aztreonam or cefaperazone; metronidazole and nystatin.

3. The method of claim 1, wherein said bacteria composition consists *essentially of Bacteroides caccae, distasonis, fragilis, stercoris, thetaiotaomicron, uniformis, vulgatus; Bifidobacterium adolescentis, longum coprococcus eutactus; Eubacterium aerofaciens, rectale; Fusobacterium prausnitzii; Lactobacillus acidophilus; Ruminococcus gnavus, bromii, obeum; Streptococcus intermedius, oralis, salivarius* and *Veillonella parvula.*

* * * * *